(12) United States Patent
Kelly et al.

(10) Patent No.: US 11,813,411 B2
(45) Date of Patent: Nov. 14, 2023

(54) DUAL LUMEN CANNULA WITH ADJUSTABLE LENGTH INFUSION TUBE

(71) Applicant: CardiacAssist, Inc., Pittsburgh, PA (US)

(72) Inventors: Patrick A. Kelly, North Huntingdon, PA (US); Jerry Stokes, Sarver, PA (US); Robert G Svitek, Freeport, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 536 days.

(21) Appl. No.: 16/917,253

(22) Filed: Jun. 30, 2020

(65) Prior Publication Data

US 2021/0402138 A1 Dec. 30, 2021

(51) Int. Cl.
| | |
|---|---|
| *A61M 1/36* | (2006.01) |
| *A61M 25/00* | (2006.01) |
| *A61M 60/00* | (2021.01) |
| *A61M 39/10* | (2006.01) |

(52) U.S. Cl.
CPC ...... *A61M 25/0026* (2013.01); *A61M 1/3659* (2014.02); *A61M 25/007* (2013.01); *A61M 39/105* (2013.01); *A61M 60/00* (2021.01); *A61M 2025/0031* (2013.01); *A61M 2025/0039* (2013.01)

(58) Field of Classification Search
None
See application file for complete search history.

(56) References Cited

U.S. PATENT DOCUMENTS

| | | | | |
|---|---|---|---|---|
| 4,819,637 | A | * | 4/1989 | Dormandy, Jr. ... A61B 17/1219 604/537 |
| 8,992,408 | B2 | | 3/2015 | Magovern et al. |
| 9,168,352 | B2 | | 10/2015 | Kelly et al. |
| 9,446,183 | B2 | | 9/2016 | Smith et al. |
| 9,782,534 | B2 | | 10/2017 | Kelly et al. |
| 10,279,101 | B2 | | 5/2019 | Kelly et al. |
| 10,603,422 | B2 | | 3/2020 | Marous, III et al. |
| 2002/0010411 | A1 | * | 1/2002 | Macoviak ........... A61M 1/3659 604/8 |
| 2002/0177822 | A1 | * | 11/2002 | St. Cyr ............... A61M 1/3653 604/264 |

(Continued)

FOREIGN PATENT DOCUMENTS

WO 2019241522 A1 12/2019

*Primary Examiner* — Ankit D Tejani
(74) *Attorney, Agent, or Firm* — Seager, Tufte & Wickhem LLP

(57) ABSTRACT

A dual lumen coaxial cannula assembly including a first infusion tube having a proximal end, a distal end, and a sidewall extending circumferentially therebetween, as well as a second drainage tube co-axially aligned with the first infusion tube, the second drainage tube having a proximal end, a distal end, and a sidewall extending circumferentially therebetween. The assembly also includes a connector assembly, which has an inlet portion through which a portion of the first infusion tube is configured to extend and an outlet portion through which a portion of the second drainage tube is configured to extend. The connector assembly is configured to enable selective axial displacement of the first infusion tube through the second drainage tube.

16 Claims, 6 Drawing Sheets

(56) References Cited

U.S. PATENT DOCUMENTS

2013/0158338 A1* 6/2013 Kelly .................. A61M 25/007
                                                    600/16
2017/0014159 A1   1/2017 Stokes et al.
2017/0043126 A1*  2/2017 Jones .................. A61M 39/045
2018/0078688 A1   3/2018 Svitek et al.
2019/0351107 A1* 11/2019 Sawhney ......... A61B 17/12186

* cited by examiner

DUAL LUMEN CANNULA WITH ADJUSTABLE LENGTH INFUSION TUBE

BACKGROUND

Field

The present disclosure generally relates to devices and methods for assisting a patient's heart with a cannula. More specifically, the present disclosure is related to a dual lumen cannula assembly having an adjustable length infusion tube, as well as to methods for assisting a patient's heart with a cannula assembly.

Description of the Related Art

Traditional cannulae used for patient life support generally involve single lumen cannulae at multiple insertion sites, high volume circuits, and cannulae that are not capable of long-term use. Multiple insertion sites increase the risk of bleeding, vessel damage, and infection, as well as pain and discomfort to the patient. These cannulae are designed and built for short-term acute therapies. Additionally, traditional cannulae usually require access sites located in the patient's groin area near the right or left femoral veins.

While multi-lumen cannula assemblies exist in the art in order to avoid the need for multiple insertion sites, the infusion tube and the drainage tube of these cannula assemblies are generally fixed in length relative to one another, as the infusion tube is affixed to the assembly by way of, e.g., an adhesive. This fixed length of the infusion tube relative to the drainage tube may limit the adjustability of cannula assembly placement within the patient's body, thereby making it difficult for the user to account for differences in patient size and/or patient vessel length when positioning the cannula assembly.

Examples of existing cannula devices are described in U.S. Pat. Nos. 9,168,352, 9,782,534, and 10,279,101, the disclosures of which are hereby incorporated by reference in their entireties.

SUMMARY

In view of the foregoing, there exists a need for a dual lumen cannula capable of enabling adjustability in the length of an inner infusion tube relative to the outer drainage tube.

Embodiments of the present disclosure are directed to a dual lumen coaxial cannula assembly. The assembly includes a first infusion tube having a first elongate body defining a first lumen therethrough, the first infusion tube having a proximal end, a distal end, and a sidewall extending circumferentially therebetween. The assembly also includes a second drainage tube co-axially aligned with the first infusion tube and having a second elongate body with a second lumen defined by a space between the first infusion tube and second drainage tube, the second drainage tube having a proximal end, a distal end, and a sidewall extending circumferentially therebetween. The assembly further includes a connector assembly, wherein the connector assembly includes an inlet portion through which a portion of the first infusion tube is configured to extend and outlet portion through which a portion of the second drainage tube is configured to extend. Additionally, the connector assembly is configured to enable selective axial displacement of the first infusion tube through the second drainage tube.

In some embodiments, the connector assembly includes a first valve positioned circumferentially around a portion of the first infusion tube to secure the first infusion tube relative to the connector assembly.

In some embodiments, the first valve is configured as a passive valve.

In some embodiments, the first valve is an O-ring.

In some embodiments, the connector assembly includes a second valve positioned circumferentially around another portion of the first infusion tube to secure the first infusion tube relative to the connector assembly.

In some embodiments, the second valve is configured as an active valve.

In some embodiments, the second valve is a Tuohy-Borst valve.

In some embodiments, the second valve includes at least one sensor configured to provide feedback regarding the securement of the first infusion tube relative to the second valve.

In some embodiments, the at least one sensor includes at least one of a pressure transducer and an axial force strain gauge.

In some embodiments, the assembly further includes a side-port connection positioned between the first valve and the second valve of the connector assembly.

In some embodiments, the assembly further includes an embolic protection device positioned between the first valve and the second valve of the connector assembly.

In some embodiments, the first infusion tube includes at least a first magnet of a first polarity and a second magnet of the first polarity positioned along the first elongate body, and further wherein the second drainage tube comprises a third magnet of a second polarity positioned proximate to a distal end thereof.

In some embodiments, the first magnet is positioned to represent a distal length limit of the first infusion tube and the second magnet is positioned to represent a proximal length limit of the first infusion tube.

In some embodiments, the assembly further includes at least one intermediate magnet positioned between the first magnet and the second magnet on the first infusion tube.

In some embodiments, the first infusion tube includes a plurality of infusion apertures provided at the distal end, the infusion apertures extending through the sidewall of the first infusion tube.

In some embodiments, the second drainage tube includes a plurality of drainage apertures provided at the distal end, the drainage apertures extending through the sidewall of the second drainage tube.

Other embodiments of the present disclosure are directed to a method of assisting a patient's heart. The method includes providing a dual lumen coaxial cannula assembly including a first infusion tube having a first elongate body defining a first lumen therethrough, the first infusion tube having a proximal end, a distal end, and a sidewall extending circumferentially therebetween, a second drainage tube co-axially aligned with the first infusion tube and having a second elongate body with a second lumen defined by a space between the first infusion tube and second drainage tube, the second drainage tube having a proximal end, a distal end, and a sidewall extending circumferentially therebetween, and a connector assembly, wherein the connector assembly comprises an inlet portion through which a portion of the first infusion tube is configured to extend and outlet portion through which a portion of the second drainage tube is configured to extend. The connector assembly is configured to enable selective axial displacement of the first infusion tube through the second drainage tube. The method further includes inserting the dual lumen coaxial cannula into an internal jugular vein of the patient, the dual lumen coaxial cannula having a length to extend from the patient's neck area to the patient's heart. The method includes maneuvering the dual lumen coaxial cannula through the patient's vasculature such that the first distal end of the first infusion tube is at least within proximity of the patient's pulmonary artery and such that the second distal end of the second drainage tube is at least within proximity of the patient's right atrium. The method also includes adjusting an axial position of the first distal end of the first infusion tube relative to the second distal end of the second drainage tube. The method includes securing the first infusion tube in a selected axial position relative to the second drainage tube. The method further includes connecting the dual lumen coaxial cannula to a blood pump for establishing right ventricular support.

In some embodiments, securing the first infusion tube in the selected axial position includes tightening a valve around a portion of the first infusion tube, wherein the valve is positioned on the connector assembly.

In some embodiments, the method further includes providing at least a first magnet of a first polarity and a second magnet of the first polarity along the first elongate body of the first infusion tube, and providing a third magnet of a second polarity proximate to a distal end of the second drainage tube, wherein the first magnet and the second magnet provide tactile feedback regarding a position of the first infusion tube relative to the third magnet of the second drainage tube.

In some embodiments, blood from the blood pump is delivered to the patient's pulmonary artery through a plurality of infusion apertures of the first infusion tube, and blood is withdrawn from the patient's right atrium through a plurality of drainage apertures of the second drainage cannula.

Further embodiments of the present disclosure are set forth in the following numbered clauses.

Clause 1. A dual lumen coaxial cannula assembly comprising: a first infusion tube having a first elongate body defining a first lumen therethrough, the first infusion tube having a proximal end, a distal end, and a sidewall extending circumferentially therebetween; a second drainage tube co-axially aligned with the first infusion tube and having a second elongate body with a second lumen defined by a space between the first infusion tube and second drainage tube, the second drainage tube having a proximal end, a distal end, and a sidewall extending circumferentially therebetween; and a connector assembly, wherein the connector assembly comprises an inlet portion through which a portion of the first infusion tube is configured to extend and outlet portion through which a portion of the second drainage tube is configured to extend, wherein the connector assembly is configured to enable selective axial displacement of the first infusion tube through the second drainage tube.

Clause 2. The dual lumen coaxial cannula assembly of clause 1, wherein the connector assembly comprises a first valve positioned circumferentially around a portion of the first infusion tube to secure the first infusion tube relative to the connector assembly.

Clause 3. The dual lumen coaxial cannula assembly of clause 2, wherein the first valve is configured as a passive valve.

Clause 4. The dual lumen coaxial cannula assembly of clause 3, wherein the first valve is an O-ring.

Clause 5. The dual lumen coaxial cannula assembly of clause 2, wherein the connector assembly comprises a second valve positioned circumferentially around another portion of the first infusion tube to secure the first infusion tube relative to the connector assembly.

Clause 6. The dual lumen coaxial cannula assembly of clause 5, wherein the second valve is configured as an active valve.

Clause 7. The dual lumen coaxial cannula assembly of clause 6, wherein the second valve is a Tuohy-Borst valve.

Clause 8. The dual lumen coaxial cannula assembly of clause 5, wherein the second valve comprises at least one sensor configured to provide feedback regarding the securement of the first infusion tube relative to the second valve.

Clause 9. The dual lumen coaxial cannula assembly of clause 8, wherein the at least one sensor comprises at least one of a pressure transducer and an axial force strain gauge.

Clause 10. The dual lumen coaxial cannula assembly of clause 5, further comprising a side-port connection positioned between the first valve and the second valve of the connector assembly.

Clause 11. The dual lumen coaxial assembly of clause 5, further comprising an embolic protection device positioned between the first valve and the second valve of the connector assembly.

Clause 12. The dual lumen coaxial assembly of clause 1, wherein the first infusion tube comprises at least a first magnet of a first polarity and a second magnet of the first polarity positioned along the first elongate body, and further wherein the second drainage tube comprises a third magnet of a second polarity positioned proximate to a distal end thereof.

Clause 13. The dual lumen coaxial assembly of clause 12, wherein the first magnet is positioned to represent a distal length limit of the first infusion tube and the second magnet is positioned to represent a proximal length limit of the first infusion tube.

Clause 14. The dual lumen coaxial assembly of clause 12, further comprising at least one intermediate magnet positioned between the first magnet and the second magnet on the first infusion tube.

Clause 15. The dual lumen coaxial cannula assembly of clause 1, wherein the first infusion tube includes a plurality of infusion apertures provided at the distal end, the infusion apertures extending through the sidewall of the first infusion tube.

Clause 16. The dual lumen coaxial cannula assembly of clause 1, wherein the second drainage tube includes a plurality of drainage apertures provided at the distal end, the drainage apertures extending through the sidewall of the second drainage tube.

Clause 17. A method of assisting a patient's heart, comprising the steps of: providing a dual lumen coaxial cannula assembly comprising: a first infusion tube having a first elongate body defining a first lumen therethrough, the first infusion tube having a proximal end, a distal end, and a sidewall extending circumferentially therebetween, a second drainage tube co-axially aligned with the first infusion tube and having a second elongate body with a second lumen defined by a space between the first infusion tube and second drainage tube, the second drainage tube having a proximal end, a distal end, and a sidewall extending circumferentially therebetween, and a connector assembly, wherein the connector assembly comprises an inlet portion through which a portion of the first infusion tube is configured to extend and outlet portion through which a portion of the second drainage tube is configured to extend, wherein the connector assembly is configured to enable selective axial displacement of the first infusion tube through the second drainage tube; inserting the dual lumen coaxial cannula into an internal jugular vein of the patient, the dual lumen coaxial cannula having a length to extend from the patient's neck area to the patient's heart; maneuvering the dual lumen coaxial cannula through the patient's vasculature such that the first distal end of the first infusion tube is at least within proximity of the patient's pulmonary artery and such that the second distal end of the second drainage tube is at least within proximity of the patient's right atrium; adjusting an axial position of the first distal end of the first infusion tube relative to the second distal end of the second drainage tube; securing the first infusion tube in a selected axial position relative to the second drainage tube; and connecting the dual lumen coaxial cannula to a blood pump for establishing right ventricular support.

Clause 18. The method of clause 17, wherein securing the first infusion tube in the selected axial position comprises tightening a valve around a portion of the first infusion tube, wherein the valve is positioned on the connector assembly.

Clause 19. The method of clause 17, further comprising providing at least a first magnet of a first polarity and a second magnet of the first polarity along the first elongate body of the first infusion tube, and providing a third magnet of a second polarity proximate to a distal end of the second drainage tube, wherein the first magnet and the second magnet provide tactile feedback regarding a position of the first infusion tube relative to the third magnet of the second drainage tube.

Clause 20. The method of clause 17, wherein blood from the blood pump is delivered to the patient's pulmonary artery through a plurality of infusion apertures of the first infusion tube, and further wherein blood is withdrawn from the patient's right atrium through a plurality of drainage apertures of the second drainage cannula.

Further details and advantages of the present disclosure will be understood from the following detailed description read in conjunction with the accompanying drawings.

DETAILED DESCRIPTION

Figure 1:
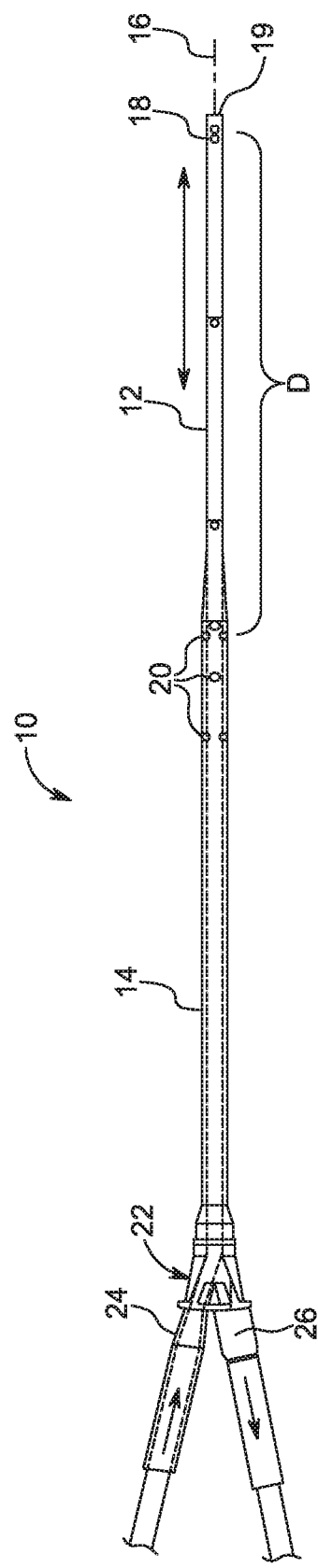
FIG. 1 is a side view of one embodiment of a coaxial cannula shown with a Y-shaped connector in accordance with an aspect of the present disclosure.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects. Hence, specific dimensions and other physical characteristics related to the embodiments or aspects disclosed herein are not to be considered as limiting.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

When used in relation to a cannula, catheter, or other device inserted into a patient, the term "proximal" refers to a portion of such device farther from the end of the device inserted into the patient. When used in relation to a cannula, catheter, or other device inserted into a patient, the term "distal" refers to a portion of such device nearer to the end of the device inserted into the patient.

Referring to the drawings, in which like reference characters refer to like parts throughout the several views thereof, various embodiments of a coaxial, dual lumen cannula 10 (hereinafter referred to as "coaxial cannula 10") are shown. With initial reference to FIG. 1, the assembled coaxial cannula 10, according to one embodiment, generally includes a first infusion tube 12 and a second drainage tube 14, with the first infusion tube 12 configured to pass through the second drainage tube 14. As will be described in further detail hereinbelow, the length of the first infusion tube 12 relative to the length of the second drainage tube 14 is configured to be adjustable so as to account for patient size and/or patient vessel length.

The first infusion tube 12 is disposed within the second drainage tube 14 in a coaxial arrangement centered about a central axis 16. Each of the first infusion tube 12 and the second drainage tube 14 has a first circumference defining a first lumen and a second circumference defining a second lumen, respectively. The first circumference of the first infusion tube 12 is smaller than the second circumference of the second drainage tube 14 such that the first infusion tube 12 may be placed within the second lumen of the second drainage tube 14. One or both of the first infusion tube 12 and the second drainage tube 14 may be manufactured from a medical-grade material such as polyurethane. Alternatively, the tubes may be made from PVC or silicone, and may be dip molded, extruded, co-molded, or made using any other suitable manufacturing technique.

The coaxial cannula 10 has sufficient placement flexibility adapted for placement of the coaxial cannula 10 within a patient's body. Desirably, a vascular insertion site is provided at the internal jugular vein on the patient's neck area. The coaxial cannula 10 is adapted for placement above or below the right atrium of the patient's heart. The coaxial cannula 10 may be used with an introducer to guide the placement of the coaxial cannula 10 as it is inserted within the patient's body.

With continuing reference to FIG. 1, the coaxial cannula 10 is designed to withdraw blood directly from the patient's heart and return blood back into the patient's heart. The function of the first infusion tube 12 is to deliver blood into the blood stream of the patient, while the function of the second drainage tube 14 is to drain the blood from the patient's bloodstream as will be described hereafter.

A plurality of infusion apertures 18 are provided near a distal end of the first infusion tube 12, and the distal end of the infusion tube includes an infusion opening 19. The plurality of infusion apertures 18 are desirably arranged in a circular pattern extending around the outer circumference of the first infusion tube 12. In some embodiments, the plurality of infusion apertures 18 may be disposed in multiple groups provided at various sites on the first infusion tube 12. Similarly, the second drainage tube 14 includes a plurality of drainage apertures 20 provided at a distal end of the second drainage tube 14. The plurality of drainage apertures 20 are desirably arranged in a circular pattern extending around the outer circumference of the second drainage tube 14. In alternative embodiments, the plurality of drainage apertures 20 may be arranged in groups disposed at various sites along the length of the second drainage tube 14.

The infusion apertures 18 are separated from the drainage apertures 20 by a variable distance D. In different embodiments of the coaxial cannula 10, the separation of infusion apertures 18 from drainage apertures 20 determines the amount of mixing of oxygenated blood and unoxygenated blood. As will be described in further detail below, the distance D may be varied by user adjustment of first infusion tube 12 with respect to the second drainage tube 14 along the central axis 16. The user may axially displace (i.e., push or pull) the first infusion tube 12 through the second drainage tube 14 until an acceptable and desired distance D is attained. In this way, the distance D may be altered based on, e.g., the age and/or size of the patient, as well as the desired flow rates during the medical procedure where the coaxial cannula 10 is used. For example, a distance D may be varied between 5 cm and 30 cm. More specifically, in some embodiments, the distance D may be varied between 8 cm and 28 cm. However, it is to be understood that the distance D is not limited to these lengths, and may be varied between lengths lesser or greater than those described herein.

With continuing reference to FIG. 1, a Y-shaped connector assembly 22 is provided at the proximal end of the coaxial cannula 10. Portions of the Y-shaped connector assembly 22 may be made substantially from polycarbonate as an example, but could also be made from PVC, acrylic, or polyurethane. The Y-shaped connector assembly 22 may be constructed using one or more manufacturing techniques including injection molding, machining, or dip forming. One of ordinary skill in the art will understand that a variety of other manufacturing techniques may be used for constructing the Y-shaped connector assembly 22 without departing from the intended scope of the invention. Additionally, while a connector assembly 22 is shown and described herein as being Y-shaped, it is to be understood that connector assembly 22 may be formed in other shapes and configurations.

The Y-shaped connector assembly 22 includes an inlet portion 24 in fluid communication with the first infusion tube 12 to transfer blood from a blood pump (not shown) to the first infusion tube 12. An outlet portion 26 of the Y-shaped connector assembly 22 is in fluid communication with the second drainage tube 14 to transfer blood from the second drainage tube 14 to the blood pump. The outlet portion 26 and the inlet portion 24 of the Y-shaped connector assembly 22 are arranged such that the fluid pathways leading from the second drainage tube 14 and to the first infusion tube 12 transition from a coaxial arrangement at a distal end of the Y-shaped connector assembly 22 to an axially-offset arrangement at a proximal end of the Y-shaped connector assembly 22.

Figure 2:
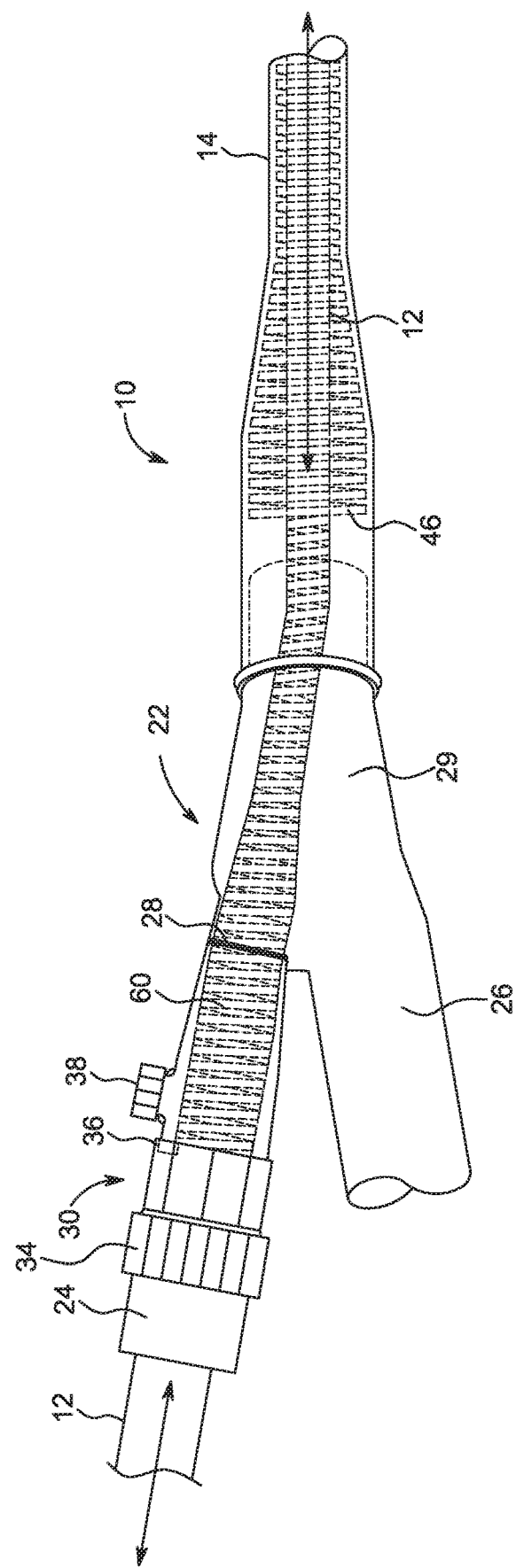
FIG. 2 is a perspective view of the Y-shaped connector shown coupled to the coaxial cannula of FIG. 1.

Referring to FIG. 2, the details of Y-shaped connector assembly 22 and the coupling of coaxial cannula 10 with Y-shaped connector assembly 22 are shown. As described above, the first infusion tube 12 is configured to extend through inlet portion 24 of Y-shaped connector assembly 22, while the outlet portion 26 acts as the fluid pathway for second drainage tube 14. The first infusion tube 12 is configured to be capable of user-controlled axial displacement through inlet portion 24 in both the distal and proximal directions. That is, the user may feed the first infusion tube 12 through the inlet portion 24 and the second drainage tube 14 in the distal direction, thereby increasing the length of the first infusion tube 12 relative to the distal end of the second drainage tube 14. Conversely, if the user pulls the first infusion tube 12 in the proximal direction, the length of the first infusion tube 12 relative to the distal end of the second drainage tube 14 decreases. Accordingly, the Y-shaped connector assembly 22 and coaxial cannula 10 enables user adjustment of the length of the first infusion tube 12 relative to the second drainage tube 14.

In one embodiment, the first infusion tube 12 includes a first helical coil 60 extending through at least a portion of the length thereof, while the second drainage tube 14 includes a second helical coil 46 extending through at least a portion of the length thereof. The first helical coil 60 and/or the second helical coil 46 may be manufactured from medical-grade metal or plastic and may act to minimize kinking and/or collapse of the first infusion tube 12 and/or the second drainage tube 14.

In addition to serving as a junction for the first infusion tube and second drainage tube 14 to form coaxial cannula 10, the Y-shaped connector assembly 22 further includes a valve system configured to both control movement of first infusion tube 12 and enable blood management by, e.g., minimizing thrombus formation, controlling blood loss, etc.

Specifically, as shown in FIG. 2, Y-shaped connector assembly 22 includes a distal valve 28 located at or near the location where inlet portion 24 and outlet portion 26 meet to form a common lumen portion 29. The distal valve 28 is positioned and configured to provide a smooth transition between the inlet portion 24 and the common lumen portion 29 of Y-shaped connector assembly 22, thereby minimizing blood flow disruption and potential thrombus formation due to such blood flow disruption.

Additionally, distal valve 28 is configured to at least partially secure the first infusion tube 12 relative to the Y-shaped connector assembly 22, while still allowing for selective axial movement of the first infusion tube 12 through the Y-shaped connector assembly 22 and the second drainage tube 14. For example, in one embodiment, distal valve 28 is configured to function passively as an O-ring, wherein the opening of the O-ring is slightly smaller in diameter than the outer diameter of first infusion tube 12. The O-ring may be formed of any appropriate medical grade material such as, e.g., polyurethane, PVC, or silicone. In this way, the O-ring forming distal valve 28 provides a friction fit over the outer diameter of first infusion tube 12, both securing the first infusion tube 12 and preventing blood to flow past distal valve 28, thereby mitigating thrombus formation, blood loss, etc. However, the friction fit of the distal valve 28 is configured to allow axial movement of first infusion tube 12 upon user-directed force on the first infusion tube 12, thereby allowing the overall length of first infusion tube 12 to be adjusted relative to second drainage tube 14, as described above.

Alternatively, in another embodiment, and in lieu of a passive configuration, distal valve 28 may be configured as an active valve incorporating, e.g., a dial or button (not shown) located outside of the Y-shaped connector assembly for manipulation by the user in order to selectively secure and/or release the first infusion tube 12.

Referring still to FIG. 2, in addition to distal valve 28, Y-shaped connector assembly 22 may further include a second, proximal valve 30 positioned along the inlet portion 24. Proximal valve 30 is configured to provide redundancy and a factor of safety with respect to securement of first infusion tube 12, working in conjunction with distal valve 28 to secure first infusion tube 12 in place once the user has positioned the first infusion tube 12 at a desired length relative to second drainage tube 14.

In one embodiment, proximal valve 30 is a manually activated valve such as, e.g., a Tuohy-Borst valve. Accordingly, proximal valve 30 includes a rotatable cap 34, which surrounds the first infusion tube 12. If the user rotates the cap 34 in a clockwise direction, an inner ring (not shown) of the proximal valve 30 compresses along the outer surface of the first infusion tube 12, thereby acting to secure the first infusion tube 12 in place. Conversely, if the user rotates the cap 34 in a counterclockwise direction, the inner ring releases from the outer surface of the first infusion tube 12, thereby allowing first infusion tube 12 to be axially displaced relative to the Y-shaped connector assembly 22. In this way, the proximal valve 30 may act as the primary means for securement of the first infusion tube 12, particularly if distal valve 28 is configured as a passive valve (e.g., an O-ring).

In addition to providing securement of the first infusion tube 12, in one embodiment, proximal valve 30 also serves as a secondary source of blood management within the Y-shaped connector assembly 22. That is, when the inner ring of the proximal valve 30 is tightened around the first infusion tube 12 in order to secure first infusion tube 12 prior to use, blood is prevented from traveling through (and potentially leaking from) the inlet portion 24 of the Y-shaped connector assembly 22. As such, thrombus formation and/or blood loss within the valve system of Y-shaped connector assembly 22 is substantially prevented, particularly when proximal valve 30 is utilized in series with distal valve 28.

The proximal valve 30 may include one or more means for providing pressure or axial force feedback indicative of a sufficient securement and/or seal around the first infusion tube 12. For example, in one embodiment, the proximal valve 30 includes at least one sensor 36, wherein the at least one sensor 36 is configured to provide feedback regarding the securement of the proximal valve 30 around the first infusion tube 12. In one embodiment, the at least one sensor 36 may be configured as a pressure transducer. In another embodiment, the at least one sensor 36 may be configured as an axial force strain gauge. The at least one sensor 36 may transmit the feedback relating to securement of the first infusion tube 12 to a remote controller and/or user interface via either a wired or wireless connection. Alternatively, the proximal valve 30 may incorporate one or more indicators (e.g., LEDs) capable of communicating the feedback from the at least one sensor 36 to the user.

In another embodiment, in lieu of (or in addition to) the distal valve 28 and/or the proximal valve 30, the Y-shaped connector assembly 22 may include a toothed ring (not shown) sized and configured to contact and surround the first infusion tube 12. The toothed ring includes a plurality of teeth directed radially inward and angled in a distal direction relative to the Y-shaped connector assembly 22. With this configuration, the toothed ring enables the first infusion tube 12 to be axially moved/adjusted in the distal direction, as the first infusion tube 12 is able to pass through the opening formed by the plurality of teeth due to the tooth angulation in the distal direction. However, the toothed ring is configured to substantially restrict or prevent movement of the first infusion tube 12 in the opposite (i.e., proximal) direction, as such movement causes the plurality of teeth to bend in the proximal direction, thereby reducing the circumference of the passage formed by the toothed ring around the first infusion tube 12, which causes the plurality of teeth to "bite" into the outer sidewall of the first infusion tube 12. In this way, the toothed ring may provide for at least supplemental securement of the first infusion tube 12 relative to the Y-shaped connector assembly 22.

Referring still to FIG. 2, and in accordance with another aspect of the present disclosure, Y-shaped connector assembly 22 further includes a side port connection 38 positioned between the distal valve 28 and the proximal valve 30. The side-port connection 38 is configured to enable proper management of the space between the respective valves 28, 30 by way of, e.g., a barb connector accessible to the user. More specifically, during initial set-up of the coaxial cannula 10, the side-port connection 38 can be utilized for de-airing the space between the respective valves 28, 30. Additionally and/or alternatively, the side-port connection 38 can be used to establish a heparin lock in the space between valves 28, 30 in order to minimize or prevent blood stasis. By injecting heparin, an anti-coagulant, into the space between the valves 28, 30 via the side-port connection 38, blood is able to flow more smoothly through the space, and potential clotting may be better prevented. Furthermore, in one embodiment, the side-port connection 38 can be used during patient support in order to manage the valve space as needed to minimize or prevent blood stasis.

Figure 3:
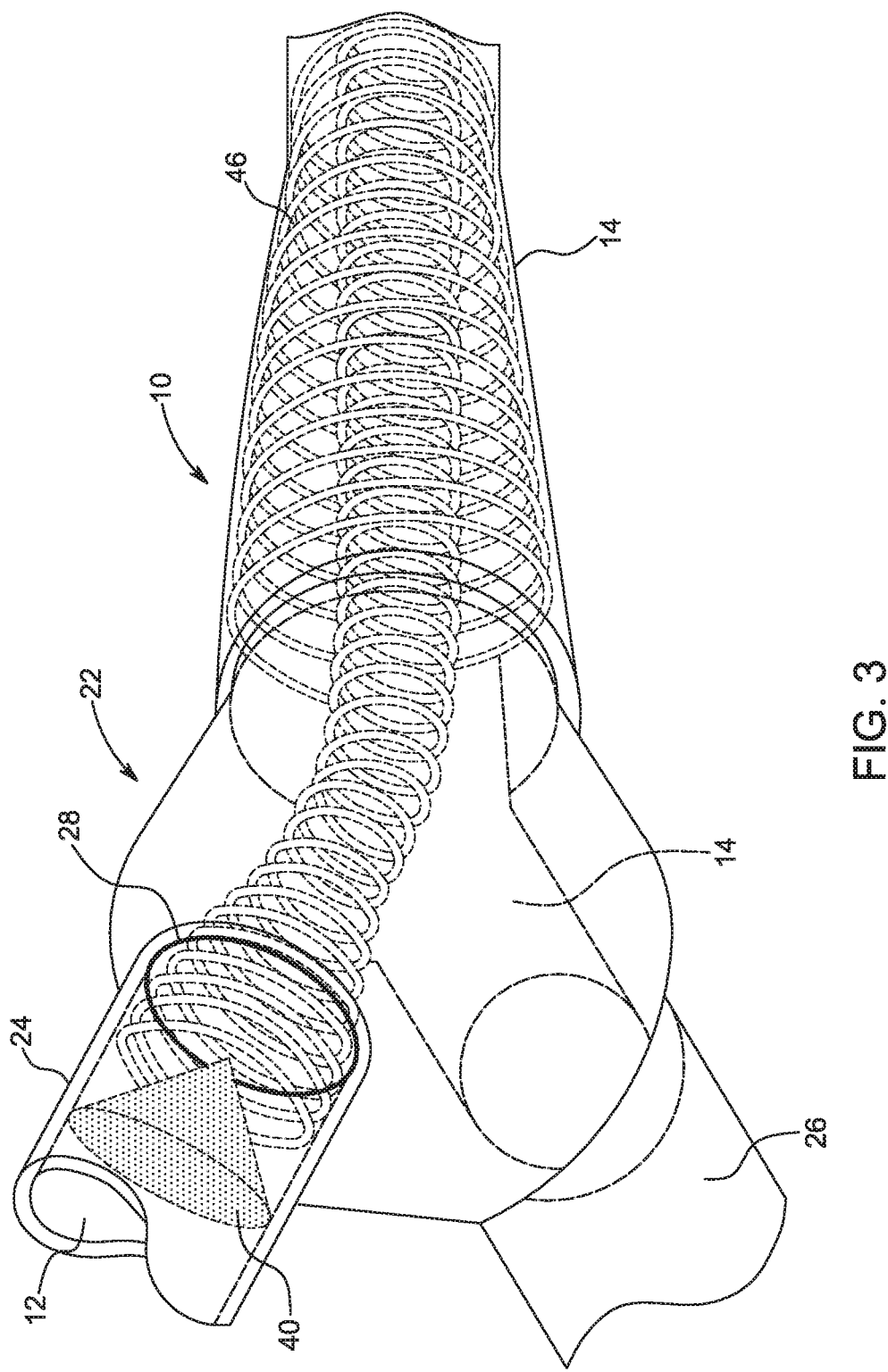
FIG. 3 is a partial perspective view of the Y-shaped connector in accordance with another aspect of the present disclosure.

Next, referring to FIG. 3, another aspect of the present disclosure with respect to Y-shaped connector assembly 22 is shown. Specifically, an embolic protection device 40 may be deployed within the valve space between respective valves 28, 30. Embolic protection device 40 may be in the form of, e.g., a filter or basket capable of capturing a thrombus or clot before the thrombus or clot enters the patient's blood stream. That is, if a thrombus or clot were to form in the space between the distal valve 28 and the proximal valve 30 of Y-shaped connector assembly 22 due to blood stasis, the embolic protection device 40 serves to substantially prevent the thrombus or clot from traveling beyond the valve space, thereby substantially reducing the risk of an embolic event. While embolic protection device 40 is shown as a filter or basket in FIG. 3, it is to be understood that embolic protection device 40 may be any appropriate device capable of filtering. Furthermore, while shown as placed in the space between the distal valve 28 and the proximal valve 30 in FIG. 3, it is to be understood that embolic protection device 40 may be situated elsewhere in the Y-shaped connector assembly 22 and/or the coaxial cannula 10.

Figure 4:
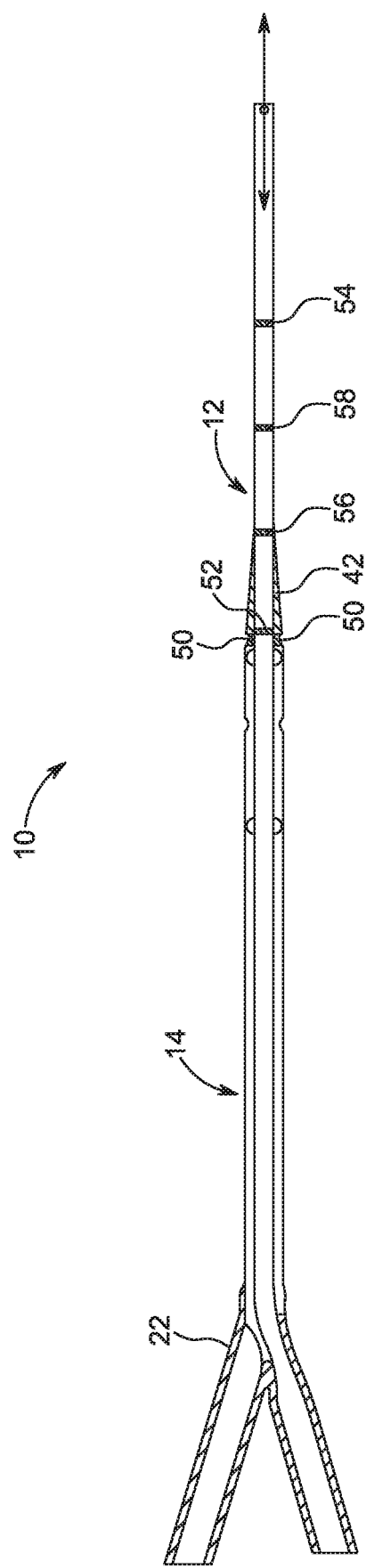
FIG. 4 is another side view of the coaxial cannula with the Y-shaped connector in accordance with an aspect of the present disclosure.

With reference to FIG. 4, another aspect of the present disclosure is shown. As described above, the first infusion tube 12 is capable of axial adjustment/movement relative to second drainage tube 14. However, in order for the user to establish the desired position of the infusion apertures 18 of the first infusion tube 12 relative to the drainage apertures 20 of the second drainage tube 14 when such axial adjustment is made with the coaxial cannula 10 within the patient's body, there is a need for the user to receive feedback as to the position of the first infusion tube 12. Accordingly, in one embodiment, the coaxial cannula 10 may include a plurality of magnets configured to provide incremental tactile feedback to the user as the first infusion tube 12 is moved through the second drainage tube 14.

Specifically, as shown in FIG. 4, the second drainage tube 14 includes a first magnet 50 having a first polarity positioned at or near a distal end portion 42 thereof. In one embodiment, the first magnet 50 may be ring-shaped and may extend circumferentially around (or within) the sidewall of the second drainage tube 14. Alternatively, the first magnet 50 may include one or more distinct magnets placed along the circumference of the second drainage tube 14. The first infusion tube 12 includes a second magnet 52, a third magnet 54, a fourth magnet 56, and a fifth magnet 58, with each of magnets 52, 54, 56, 58 having a second polarity opposite that of the first polarity of first magnet 50.

In the example shown in FIG. 4, the second magnet 52 is positioned to represent the distal length limit of first infusion tube 12 (i.e., the greatest allowable length between the distal end of the first infusion tube 12 and the distal end of the second drainage tube 14), while the third magnet 54 is positioned to represent the proximal length limit of the infusion tube 12 (i.e., the least allowable length between the distal end of the first infusion tube 12 and the distal end of the second drainage tube 14). The distal length limit of the first infusion tube 12, represented by second magnet 52, may be defined to minimize pressure drop and enable the coaxial cannula 10 to achieve blood flows needed to provide adequate circulatory support. In some embodiments, the maximum length of first infusion tube 12 may be 75 cm, while the minimum length of first infusion tube 12 may be 50 cm. However, it is to be understood that the maximum and minimum lengths of first infusion tube 12 are not limited to the above range.

The fourth magnet 56 and fifth magnet 58 are incrementally positioned between the second magnet 52 and the third magnet 54. Similar to the first magnet 50, each of magnets 52, 54, 56, 58 may be ring-shaped and may extend circumferentially around (or within) the sidewall of the first infusion tube 12. Alternatively, the magnets 52, 54, 56, 58 may include one or more distinct magnets placed along the circumference of the first infusion tube 12. Furthermore, while four total magnets are shown in FIG. 4, it is to be understood that more or fewer magnets may be utilized.

During use of the coaxial cannula 10 and axial displacement of the first infusion tube 12 relative to the second drainage tube 14, the user will receive tactile feedback as each of the magnets 52, 54, 56, 58 of the first infusion tube 12 pass the first magnet 50 of the second drainage tube 14 due to the magnets' opposing polarities. In this way, the user receives a tactile indication of the precise position of the first infusion tube 12 relative to the second drainage tube 14, including the proximal length limit (from third magnet 54) and the distal length limit (from second magnet 52). The magnets 52, 54, 56, 58 may be spaced apart at known increments (e.g., 1 cm) such that the user can precisely position and secure the first infusion tube 12 at a desired length relative to the second drainage tube 14.

While the example described with respect to FIG. 4 utilizes magnets to provide tactile feedback to the user regarding the positioning of the first infusion tube 12, it is to be understood that other forms of tactile and non-tactile feedback may be utilized for such purposes. For example, in lieu of magnets, a plurality of rings or ridges may be provided at spaced-apart locations on the first infusion tube 12, and the distal end of the second drainage tube 14 may be slightly undersized as compared to other portions of the second drainage tube 14. Thus, as the rings/ridges pass the undersized portion of the second drainage tube 14, the user would sense a slight interference fit, thereby providing for tactile feedback as the first infusion tube 12 is positioned relative to second drainage tube 14. Alternatively, instead of the rings/ridges being located near the distal end of first infusion tube 12 and the tactile feedback being provided by passage through the undersized distal end of the second drainage tube 14, the rings/ridges may be provided nearer the proximal end of the first infusion tube 12, with the undersized portion of the second drainage tube 14 also being provided at or near a proximal end thereof. With this configuration, direct blood flow over the rings/ridges on first infusion tube 12 may be avoided.

Referring still to FIG. 4, the distal end portion 42 of second drainage tube 14, illustrated as a tapered section, is configured to allow the first infusion tube 12 to move axially with respect to second drainage tube 14. In order to prevent blood flow through this tapered section, the distal end portion 42 may include one or more valves (e.g., O-rings) to substantially seal the interface between the first infusion tube 12 and the second drainage tube 14. Additionally, the one or more valves at the distal end portion 42 may function as supplemental securement devices in order to secure the first infusion tube 12 relative to the second drainage tube 14.

Figure 5:
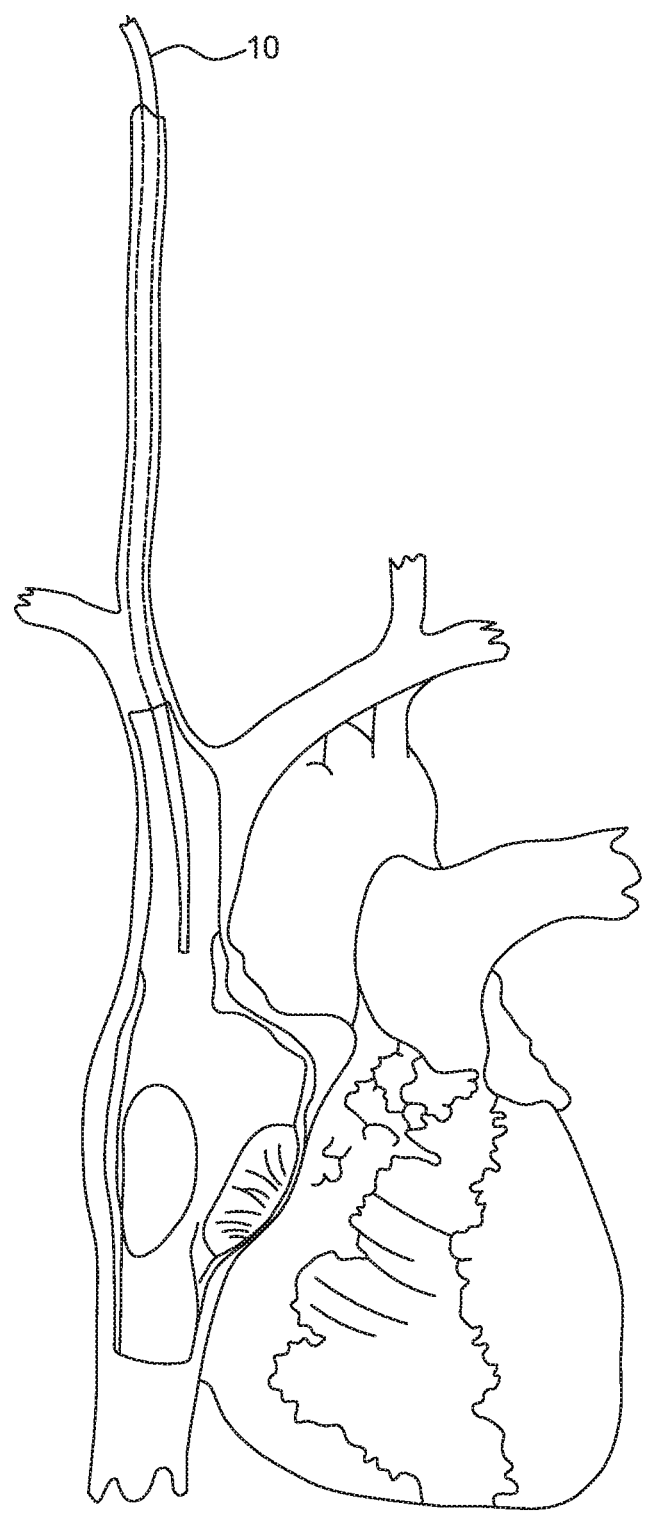
FIG. 5 is a schematic view of one embodiment of a coaxial cannula positioned inside a patient's heart.
Figure 6:
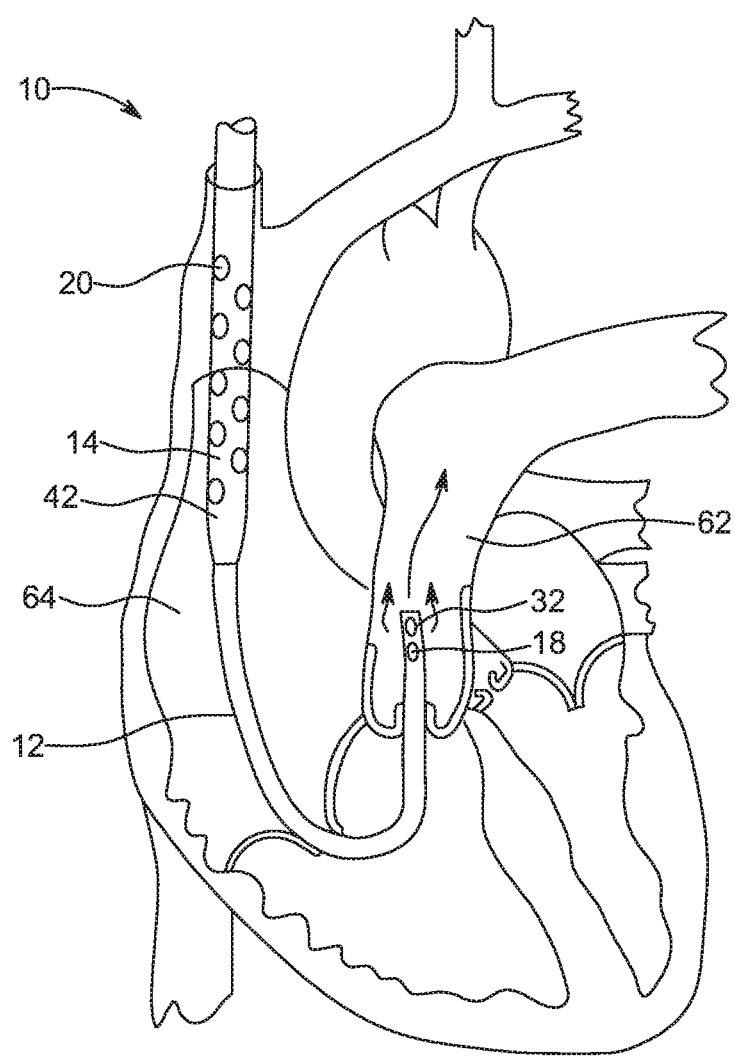
FIG. 6 is a schematic view of the coaxial cannula of any of FIGS. 1-4 positioned inside a patient's heart.

Having described several non-limiting embodiments of the coaxial cannula 10 and the Y-shaped connector assembly 22, an exemplary and non-limiting method for supporting the right heart of a patient using the coaxial cannula 10 will now be described with reference to FIGS. 5 and 6. In use, the coaxial cannula 10 is inserted into the pulmonary artery in a percutaneous procedure. Initially, a percutaneous entry needle (not shown) is used to access the patient's internal jugular vein (IJV). An introducer, such as a guidewire, is then inserted through the needle until the tip of the introducer is positioned in the upper portion of the inferior vena cava/right atrium (IVC/RA) junction. The needle can then be removed, and a pulmonary wedge catheter can be inserted over the guidewire into the pulmonary artery. The introducer tip is then threaded into the pulmonary artery, and the wedge catheter is removed. The IJV is then serially dilated and the coaxial cannula 10 is threaded along the introducer into the IJV, through the right ventricle, and into the pulmonary artery. The distal end 32 of the first infusion tube 12 is sufficiently flexible about the central axis 16 so as to navigate the IJV, right ventricle, and pulmonary artery. The coaxial cannula 10 may include insertion depth markers and radiopaque markers for aiding the user in placing the coaxial cannula 10 in the right atrium. Furthermore, as described above, the position of the first infusion tube 12 relative to the second drainage tube 14 may be adjusted by the user based on, e.g., patient size, patient vessel length, etc. Once the position of the coaxial cannula 10 is acceptable, the introducer may be removed and the coaxial cannula 10 may be clamped in place. For example, the coaxial cannula 10 may be secured to the patient's neck using a suture. FIG. 6 shows the coaxial cannula 10 positioned in the patient according to some embodiments of the disclosure. In particular, the distal end 42 of the second drainage tube 14 is positioned at least within proximity with the right atrium 64, while the distal end 32 of the first infusion tube 12 extends into the pulmonary artery 62.

While several embodiments of a coaxial cannula and connector assembly are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A dual lumen coaxial cannula assembly comprising:
   a first infusion tube having a first elongate body defining a first lumen therethrough, the first infusion tube having a proximal end, a distal end, and a sidewall extending circumferentially therebetween;
   a second drainage tube co-axially aligned with the first infusion tube and having a second elongate body with a second lumen defined by a space between the first infusion tube and second drainage tube, the second drainage tube having a proximal end, a distal end, and a sidewall extending circumferentially therebetween; and
   a connector assembly, wherein the connector assembly comprises an inlet portion through which the first infusion tube is configured to extend, an outlet portion in fluid communication with the second drainage tube, and a common lumen portion in fluid communication with and extending distally from the inlet portion and the outlet portion, the common lumen being coupled to the second drainage tube and through which the first infusion tube is configured to extend into the second drainage tube, wherein the connector assembly is configured to enable selective axial displacement of the first infusion tube through the second drainage tube;
   wherein the inlet portion is noncoaxial with the common lumen portion.

2. The dual lumen coaxial cannula assembly of claim 1, wherein the connector assembly comprises a first valve positioned circumferentially around a portion of the first infusion tube to secure the first infusion tube relative to the connector assembly.

3. The dual lumen coaxial cannula assembly of claim 2, wherein the first valve is configured as a passive valve.

4. The dual lumen coaxial cannula assembly of claim 3, wherein the first valve is an O-ring.

5. The dual lumen coaxial cannula assembly of claim 2, wherein the connector assembly comprises a second valve positioned circumferentially around another portion of the first infusion tube to secure the first infusion tube relative to the connector assembly.

6. The dual lumen coaxial cannula assembly of claim 5, wherein the second valve is configured as an active valve.

7. The dual lumen coaxial cannula assembly of claim 6, wherein the second valve is a Tuohy-Borst valve.

8. The dual lumen coaxial cannula assembly of claim 5, wherein the second valve comprises at least one sensor configured to provide feedback regarding the securement of the first infusion tube relative to the second valve.

9. The dual lumen coaxial cannula assembly of claim 8, wherein the at least one sensor comprises at least one of a pressure transducer and an axial force strain gauge.

10. The dual lumen coaxial cannula assembly of claim 5, further comprising a side-port connection positioned between the first valve and the second valve of the connector assembly.

11. The dual lumen coaxial cannula assembly of claim 5, further comprising an embolic protection device positioned between the first valve and the second valve of the connector assembly.

12. The dual lumen coaxial cannula assembly of claim 1, wherein the first infusion tube comprises at least a first magnet of a first polarity and a second magnet of the first polarity positioned along the first elongate body, and further wherein the second drainage tube comprises a third magnet of a second polarity positioned proximate to a distal end thereof.

13. The dual lumen coaxial cannula assembly of claim 12, wherein the first magnet is positioned to represent a distal length limit of the first infusion tube and the second magnet is positioned to represent a proximal length limit of the first infusion tube.

14. The dual lumen coaxial cannula assembly of claim 12, further comprising at least one intermediate magnet positioned between the first magnet and the second magnet on the first infusion tube.

15. The dual lumen coaxial cannula assembly of claim 1, wherein the first infusion tube includes a plurality of infusion apertures provided at the distal end, the infusion apertures extending through the sidewall of the first infusion tube.

16. The dual lumen coaxial cannula assembly of claim 1, wherein the second drainage tube includes a plurality of drainage apertures provided at the distal end, the drainage apertures extending through the sidewall of the second drainage tube.

* * * * *